US010810772B2

(12) United States Patent
Tibshirani et al.

(10) Patent No.: US 10,810,772 B2
(45) Date of Patent: *Oct. 20, 2020

(54) TECHNIQUES FOR DISPLAYING STACK GRAPHS

(71) Applicant: Palantir Technologies Inc., Palo Alto, CA (US)

(72) Inventors: Julie Noelle Tibshirani, Menlo Park, CA (US); Ryan Amelia Beiermeister, Washington, DC (US); Daniel Patrick Cervelli, Mountain View, CA (US); Timothy James Slatcher, Hampshire (GB); Gregory DeJuan Martin, Royal Oak, MI (US); Antoine Alexandre Adrien Llorca, San Francisco, CA (US); Timothy James Wilson, Palo Alto, CA (US)

(73) Assignee: Palantir Technologies Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/872,229

(22) Filed: May 11, 2020

(65) Prior Publication Data

US 2020/0273221 A1     Aug. 27, 2020

Related U.S. Application Data

(63) Continuation of application No. 15/090,524, filed on Apr. 4, 2016, now Pat. No. 10,650,558.

(51) Int. Cl.
*G06T 11/20* (2006.01)
*G06Q 50/22* (2018.01)
*G06Q 40/00* (2012.01)

(52) U.S. Cl.
CPC ............ *G06T 11/206* (2013.01); *G06Q 40/00* (2013.01); *G06Q 50/22* (2013.01)

(58) Field of Classification Search
CPC ........ G06T 11/00; G06T 11/20; G06T 11/206; G06Q 40/00; G06Q 50/22; G06F 3/0481; G01R 13/405; G09G 1/162; H04L 5/0067
USPC ...................................................... 345/440
See application file for complete search history.

(56) References Cited

U.S. PATENT DOCUMENTS

| 5,842,173 | A  | * | 11/1998 | Strum ..................... | G16H 10/60 705/2 |
| 2003/0061072 | A1 | * | 3/2003 | Baker ..................... | G06Q 50/24 705/3 |
| 2005/0215867 | A1 | * | 9/2005 | Grigsby ................. | G16H 40/20 600/300 |
| 2009/0106652 | A1 | * | 4/2009 | Stluka .................... | G06Q 10/06 715/273 |

(Continued)

OTHER PUBLICATIONS

U.S. Appl. No. 15/090,524, filed Apr. 4, 2016.

*Primary Examiner* — Sae Won Yoon
(74) *Attorney, Agent, or Firm* — Hickman Palermo Becker Bingham LLP

(57) ABSTRACT

A method and system for drawing a stack graph that includes a timeline and one or more stack lines based on a set of event data. A stack line may be associated with an event target and may include one or more event overlays that represent event objects. In one implementation, event overlays may include a visual characteristic that identifies an event source associated with the event object of the event overlay.

20 Claims, 13 Drawing Sheets

(56) References Cited

U.S. PATENT DOCUMENTS

| | | | |
|---|---|---|---|
| 2012/0166208 A1* | 6/2012 | Gillam | G06Q 10/06 |
| | | | 705/2 |
| 2013/0231953 A1* | 9/2013 | Ebadollahi | G06Q 50/22 |
| | | | 705/3 |
| 2014/0149129 A1* | 5/2014 | Getchius | G06Q 50/22 |
| | | | 705/2 |
| 2015/0066939 A1* | 3/2015 | Misra | G06F 16/355 |
| | | | 707/739 |
| 2015/0220638 A1* | 8/2015 | Motoyama | G06F 16/332 |
| | | | 707/722 |
| 2015/0220868 A1* | 8/2015 | Elashoff | G06Q 50/22 |
| | | | 705/2 |
| 2016/0217218 A1* | 7/2016 | Hong | G06Q 10/06 |

\* cited by examiner

TECHNIQUES FOR DISPLAYING STACK GRAPHS

CROSS-REFERENCE TO RELATED APPLICATIONS

Benefit Claim

This application claims the benefit as a Continuation of application Ser. No. 15/090,524, filed Apr. 4, 2016, the entire contents of which is hereby incorporated by reference as if fully set forth herein, under 35 U.S.C. § 120. The applicant(s) hereby rescind any disclaimer of claim scope in the parent application(s) or the prosecution history thereof and advise the USPTO that the claims in this application may be broader than any claim in the parent application(s).

TECHNICAL FIELD

The present Application relates to graphical user interfaces for computer systems. More specifically, the example embodiment(s) of the present invention described below relate to displaying a stack graph.

BACKGROUND

It is challenging to detect patterns in a large data set that represents events that occurred between sources and targets over time. In particular, it can be difficult to identify a small subset of data that represents an abnormal pattern from a large data set over a temporal period. Identifying such a pattern is akin to finding a "needle in a haystack." It would be helpful to be able to visually organize the large data set so that the pattern is more readily identifiable. Such techniques can be helpful in identifying patterns in various practical application areas, including detecting healthcare fraud and insider trading.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

The example embodiment(s) of the present invention are illustrated by way of example, and not in way by limitation, in the figures of the accompanying drawings and in which like reference numerals refer to similar elements and in which.

DESCRIPTION OF THE EXAMPLE EMBODIMENT(S)

In the following description, for the purposes of explanation, numerous specific details are set forth in order to provide a thorough understanding of the example embodiment(s) of the present invention. It will be apparent, however, that the example embodiment(s) may be practiced without these specific details. In other instances, well-known structures and devices are shown in block diagram form in order to avoid unnecessarily obscuring the example embodiment(s).

It can be difficult to provide a graphical user interface that enables a user to easily identify a small subset of data that represents an abnormal pattern from a large data set over a temporal period. It would be helpful to be able to visually organize the large data set so that the pattern is more readily identifiable. The techniques described herein describe displaying a stack graph for a set of event data. In this context, a "stack graph" may be defined as a graphical representation of event data that organizes the event data into one or more stack lines, as further described herein. A stack graph organizes the event data so that it is easier to identify a pattern in the event data. As is explained in greater detail elsewhere in this description, a stack line is a graphical representation of event objects that are related to an event target over a time period.

Structural Overview

Figure 1:
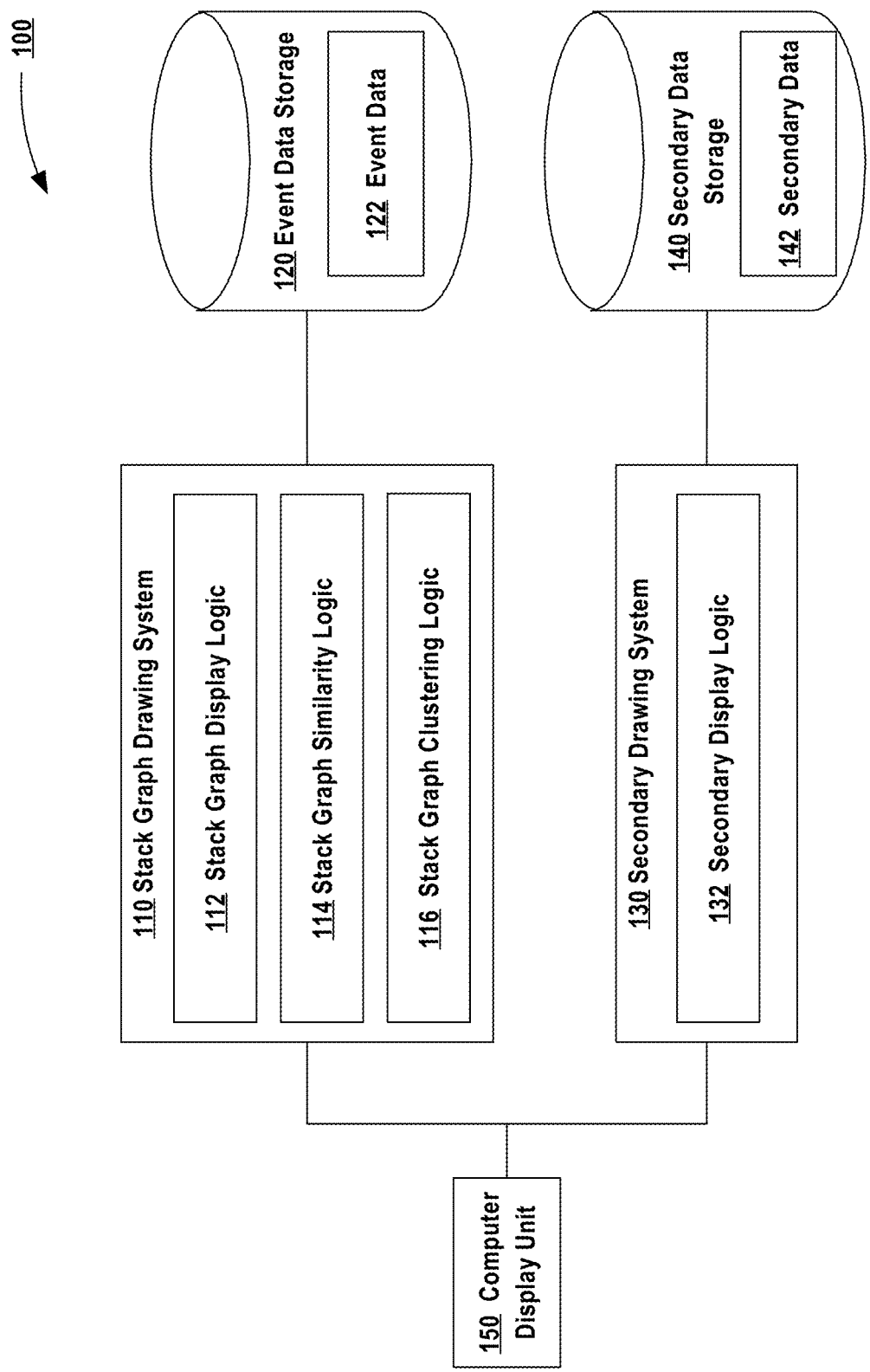
FIG. 1 is a block diagram of an example drawing system.

Techniques for displaying a stack graph may be embodied in virtually any type of computer system, including, in one embodiment, a computer system such as drawing system 100 of FIG. 1. Drawing system 100 includes stack graph drawing system 110. Stack graph drawing system 110 is a system capable of drawing a stack graph, and may include stack graph display logic 112, stack graph distance logic 114, and/or stack graph clustering logic 116. Stack graph display logic 112 is configured to transform a set of event data 122 into instructions for displaying a stack graph that includes a timeline and one or more stack lines. Stack graph distance logic 114 is configured to determine a distance score between a pair of stack lines in a stack graph. Stack graph clustering logic 116 is configured to identify a group of stack lines that should be clustered together in a stack graph. Stack graph drawing system 110 may be coupled to a computer display unit 150. Stack graph drawing system 110 may also be coupled to event data storage 120 storing event data 122.

In one embodiment, drawing system 100 may further include secondary drawing system 130. Secondary drawing system 130 is a system capable of drawing a secondary graph or secondary table, and may include secondary display logic 132. Secondary display logic 132 is configured to transform a set of secondary data 142 into instructions for displaying a secondary graph or secondary table. Secondary drawing system may be coupled to a computer display unit 150. Secondary drawing system 130 may also be coupled to secondary data storage 140 storing secondary data 142. In one embodiment, secondary drawing system 130 may be implemented as another stack graph drawing system. In one embodiment, secondary data 142 is the same as event data 122.

Stack graph drawing system 110, secondary drawing system 130, computer display unit 150, event data storage 120, and secondary data storage 140 may be implemented by the same computer system. Alternatively, stack graph drawing system 110, secondary drawing system 130, computer display unit 150, event data storage 120, and secondary data storage 140 may be implemented by a plurality of computer systems arranged in any convenient manner, such as a two-tier client/server architecture or a three-tier architecture that includes, for example, a client tier including computer display unit 150, an application tier including stack graph drawing system 110 and/or secondary drawing system 130, and a database tier including event data storage 120 and/or secondary data storage 140.

Figure 2:
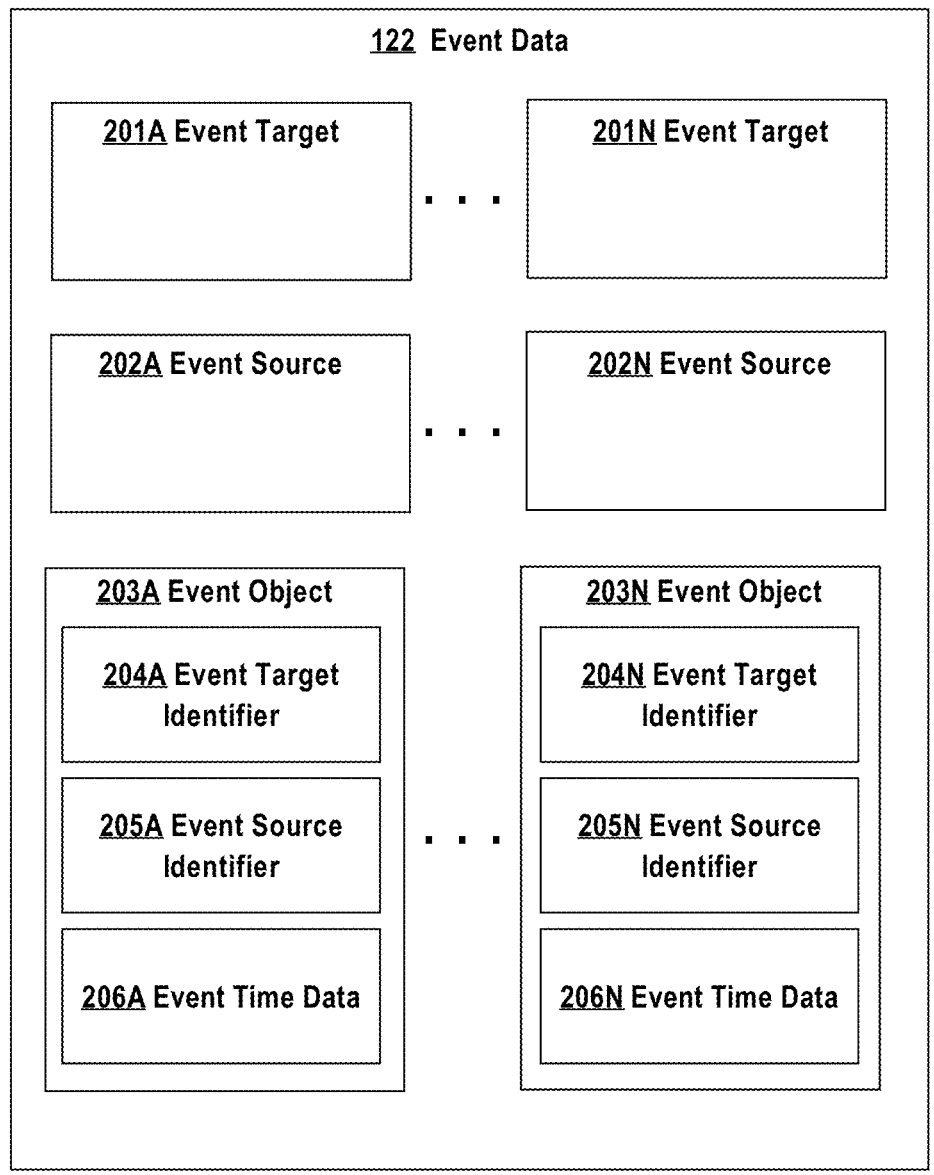
FIG. 2 is a diagram of an example of event data.

FIG. 2 shows an example of event data 122, according to one embodiment. Event data is a set of data that describes one or more events, where an event is relationship between an event target and an event source, where the relationship includes a temporal component. Event data 122 includes a plurality of event targets 201A through 201N. An event target is a data object that indicates the target of an event. Event data 122 includes a plurality of event sources 202A through 202N. An event source is a data object that indicates the source of an event. Event data 122 includes a plurality of event objects 203A through 203N. An event object is a data object that represents an event that occurred, is occurring, or will occur. In another embodiment, an event object is a data object that represents a relationship between an event source and an event target. An event object includes one or more event target identifiers that indicate the target of the event object. For example, event object 203A includes event target identifier 204A, and event object 203N includes event target identifier 204N. Thus, an event object 203 is related to the event target identified by the one or more event target identifiers 204. An event object includes one or more event source identifiers that indicate the source of the event object. For example, event object 203A includes event source identifier 205A, and event object 203N includes event source identifier 205N. Thus, an event object 203 is related to the event source identified by the one or more event source identifiers 205. An event object includes event time data. Event time data is a data object that indicates the point(s) in time or period of time when the event object occurred. For example, event object 203A includes event time data 206A, and event object 203N includes event time data 206N. In one embodiment, event time data includes an event start time and/or an event end time. Therefore, an event object 203 defines an event between an event target identified by event target identifier 204 and an event source identified by event source identifier 205 at a time identified by event time data 206.

Functional Overview

Figure 3:
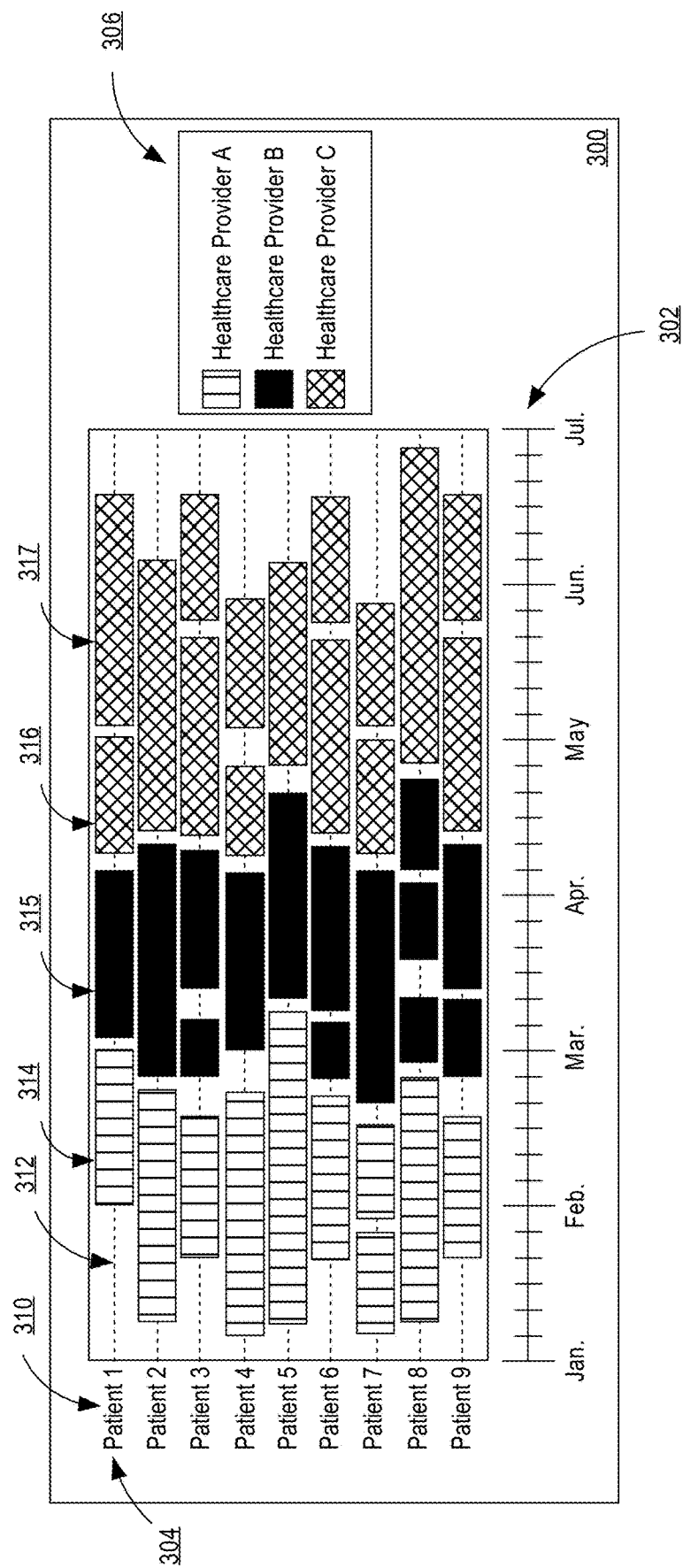
FIG. 3 is a diagram of an example stack graph.

FIG. 3 depicts an example stack graph 300 according to one embodiment. Stack graph 300 may be drawn by stack graph drawing system 110 on computer display unit 150. A stack graph includes a timeline. For example, stack graph 300 includes timeline 302. A timeline is a graphical representation of the passage of time over a time period.

A stack graph includes one or more stack lines. For example, stack graph 300 includes a one or more stack lines, such as stack line 304. A stack line is a graphical representation of event objects that are related to an event target over the time period associated with the timeline. A stack line may include a stack line event target label that indicates the event target associated with the stack line. For example, as depicted in stack graph 300, stack line 304 includes a stack line event target label 310 that indicates that the stack line is associated with an event target identified as "Patient 1". Additional stack lines exist in stack graph 300 for additional event targets, such as "Patient 2", "Patient 3", "Patient 4", etc.

Stack line 304 includes an event line 312 that graphically represents the event target of the stack line over the time period associated with the timeline 302. Although the event line 312 is depicted as a dotted line in stack graph 300, event line 312 may alternatively be depicted as any type of line or may be invisible. Additionally, although FIG. 3 depicts a horizontal event line 312, it is possible to implement these techniques with an event line of any orientation.

Stack line 304 includes event overlays 314, 315, 316, and 317. In this context, an "event overlay" may be defined as a graphical representation of an event object that is displayed on or near an event line, as is described further herein. An event overlay is related to the event target of a stack line. For example, event overlay 314 is a graphical representation of an event object associated with "Patient 1", and event overlay 315 is a graphical representation of another event object associated with "Patient 1". An event overlay is displayed on the event line of a stack line. Thus, event overlays 314, 315, 316, and 317 are each displayed on event line 312 of stack line 304. In one embodiment, the position and/or size of an event overlay corresponds to the event time data associated with the event object that the event overlay represents, thus allowing the event overlays to be correlated to the timeline of the stack graph. For example, as shown in stack graph 300, the event time data associated with the event object of event overlay 314 begins at the beginning of February and ends at the beginning of March, as can be determined by looking at timeline 302. Thus, a user that is viewing a stack graph can use the timeline and the size and/or position of the event overlays to understand the timing of the event objects that are associated with a particular event target. Although stack graph 300 depicts discrete event overlays 314, 315, 316, and 317, in another embodiment, the event overlays may overlap if the event time data associated with the event objects of the event overlays overlap in time. Additionally, although stack graph 300 depicts event overlays 314, 315, 316, and 317 that occur over a period of time, it is possible that event overlays may, in another embodiment, be depicted as points on the event line of a stack line if the event time data for the event objects represents a specific point in time as opposed to time period.

An event overlay may include one or more visual characteristics that identify a particular event source that corresponds to the event object associated with the event overlay. Thus, for example, in stack graph 300, the event overlays 314, 315, 316, and 317 have background shading that identifies the particular event source that corresponds to each event object associated with each even overlay. Stack graph 300 may include a legend 306 that provides information regarding the visual characteristics that identify a particular event source in the stack graph. Thus, by looking at legend 306, it is possible to determine based on these visual characteristics that event overlay 314 is associated with an event source "Healthcare Provider A", event overlay 315 is associated with an event source "Healthcare Provider B", and event overlays 316 and 317 are associated with an event source "Healthcare Provider C". A visual characteristic of an event overlay can be any visual characteristic that allows a user to visually distinguish between event overlays that are associated with a different event source. Examples of visual characteristics that may be used include, but are not limited to, shading of the event overlay, border style of the event overlay (e.g., border thickness, dotted lines, etc.), shape of the event overlay, border color of the event overlay, fill color of the event overlay (e.g. color-coding), transparency of the event overlay, or a label on the event overlay.

In one embodiment, an event overlay can display additional information regarding the event object in a pop-up window when a user input interacts with the event overlay, such as with a mouse-over or touch gesture.

Secondary Table and Secondary Graph

Figure 4:
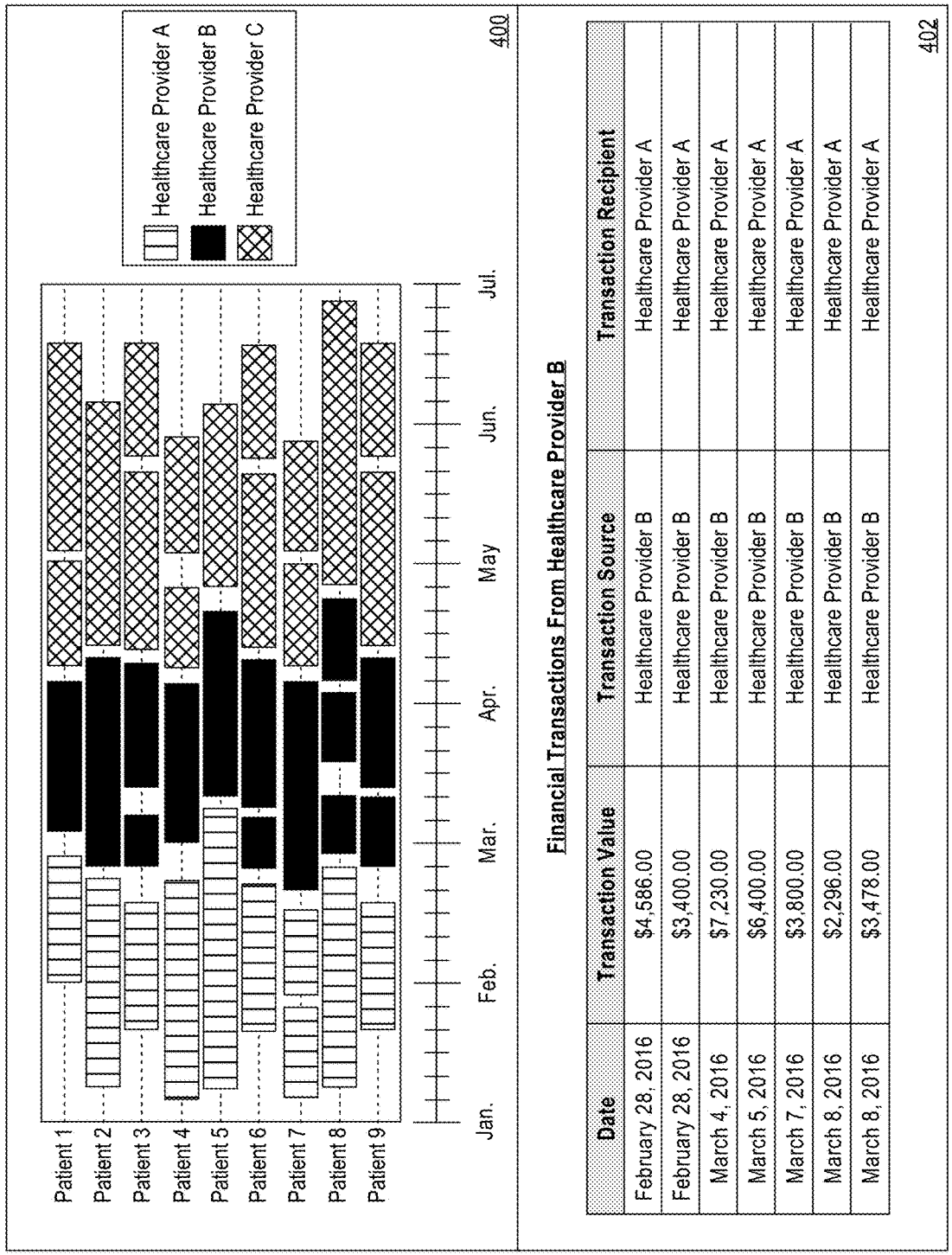
FIG. 4 is a diagram of an example stack graph and an example secondary table.

In an embodiment, drawing system 100 may display a secondary graph or secondary table in addition to a stack graph. For example, in FIG. 4, drawing system 100 may display a stack graph 400 and a secondary table 402. Secondary table 402, in this case, is a table that details financial transactions from Healthcare Provider B, an event source. Secondary display logic 132 of secondary drawing system 130 is configured to transform a set of secondary data 142 into instructions for displaying a secondary table, such as secondary table 402. In one embodiment, secondary data 142 is the same as event data 122. The format and contents of the secondary table 402 can take any format or style. In an embodiment, the time range of entries in the secondary table 402 is correlated with the timeline of the stack graph such that the secondary table 402 only displays entries that occurred during the time period associated with the timeline of the stack graph 400. By displaying secondary table 402 in conjunction with stack graph 400, the drawing system 100 allows a user to easily cross correlate event data secondary data that are formatted differently in order to see and understand patterns that may be important in the event data and secondary data.

Figure 5:
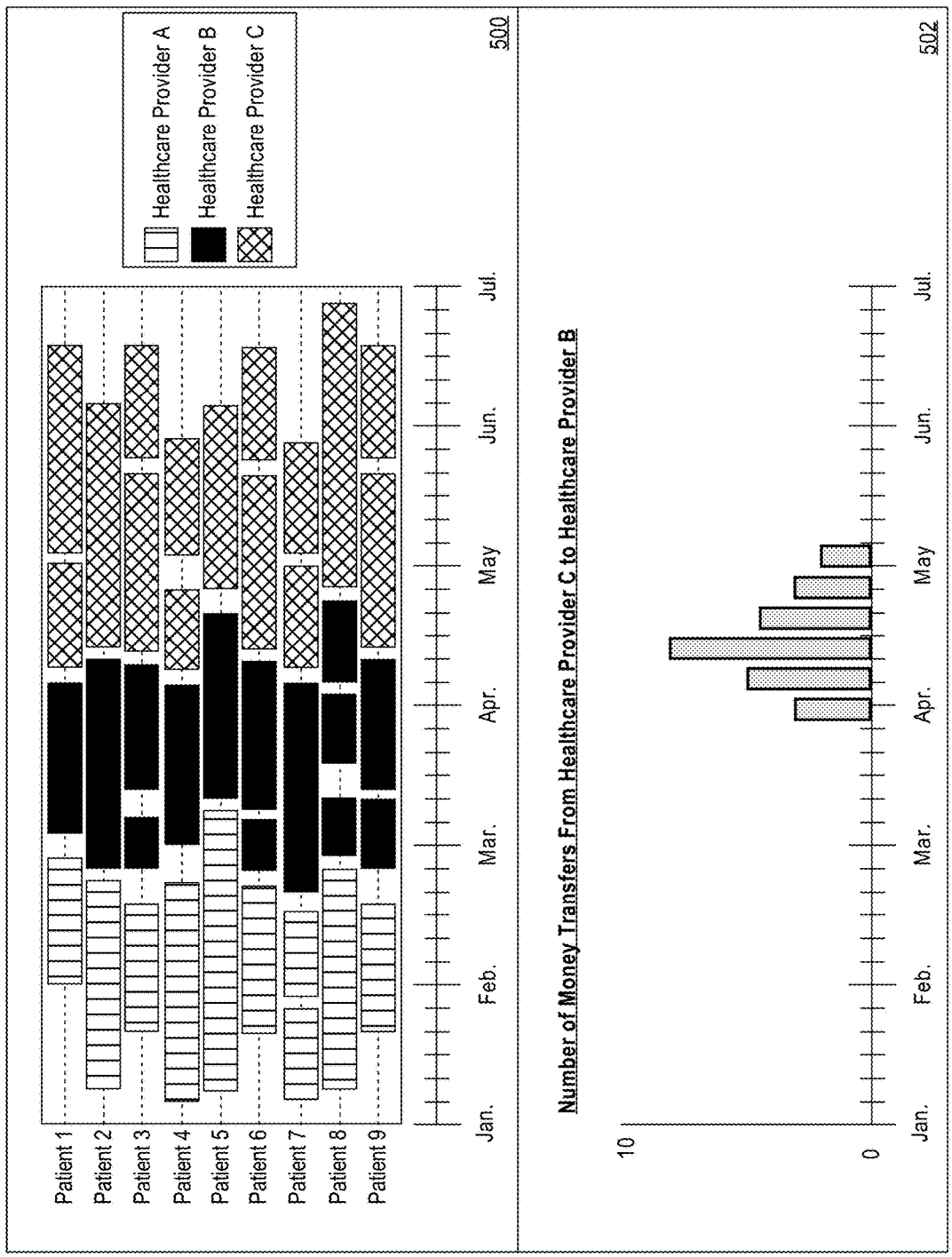
FIG. 5 is a diagram of an example stack graph and an example secondary graph.

In FIG. 5, drawing system 100 displays a stack graph 500 and a secondary graph 502. Secondary graph 502, in this case, is a bar chart that details the number of money transfers from Healthcare Provider C to Healthcare Provider B. Secondary display logic 132 of secondary drawing system 130 is configured to transform a set of secondary data 142 into instructions for displaying a secondary graph, such as secondary graph 502. Secondary graph 502 can take the form of any graph, such as a node graph, bar chart, pie chart, histogram, line graph, geographic graph or map, another stack graph, or any other type of visual representation of secondary data 142. In an embodiment, a timeline of a secondary graph is aligned with the timeline of the stack graph so that the two timelines are synchronized. By displaying secondary graph 502 in conjunction with stack graph 500, the drawing system 100 allows a user to easily cross correlate event data and secondary data that are formatted differently in order to see and understand patterns that may be important in the event data and secondary data.

Figure 13:
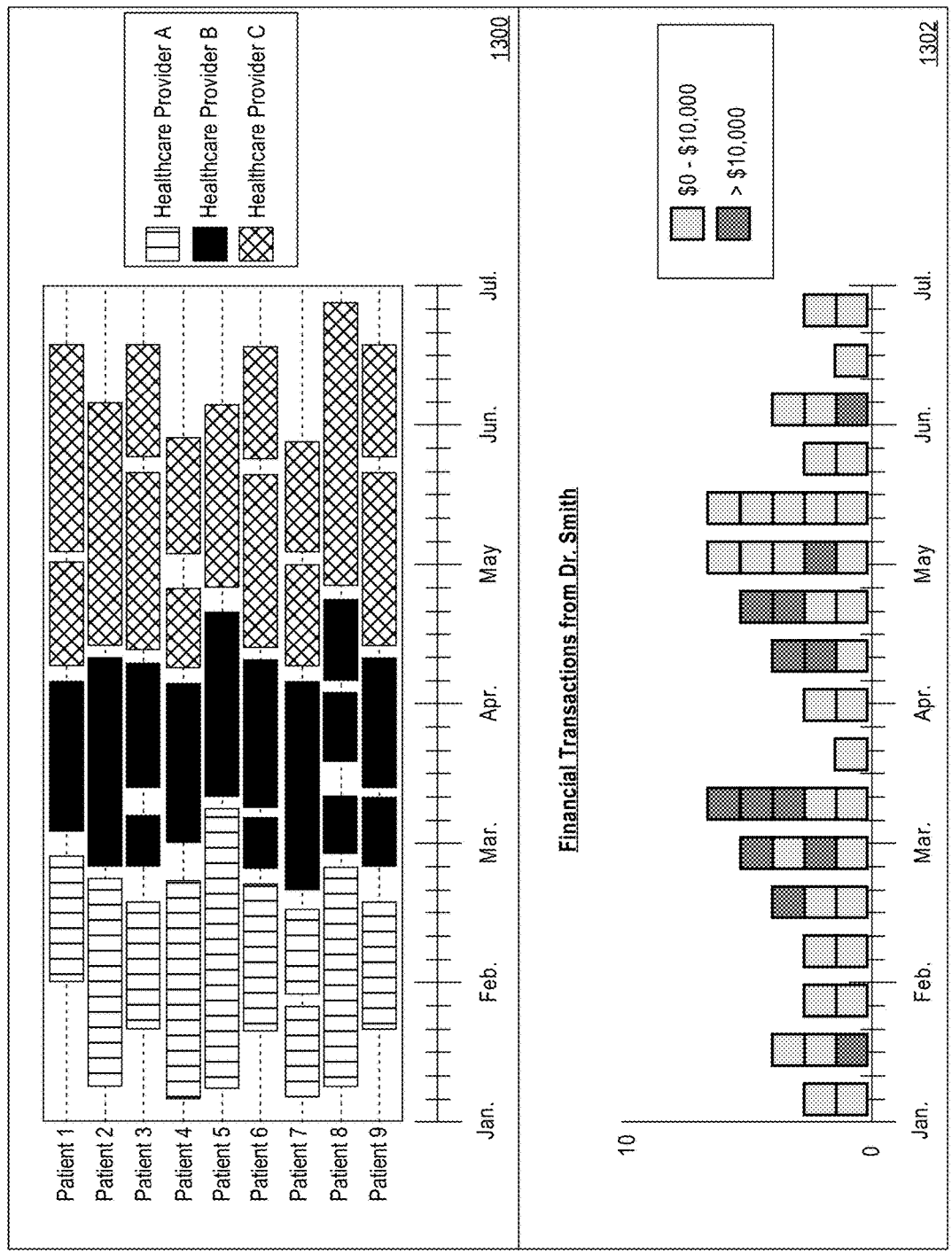
FIG. 13 is a diagram of an example stack graph and an example event block graph.

In FIG. 13, drawing system 100 displays a stack graph 1300 and an event block graph 1302. Event block graph 1302 is an example of a secondary graph. An "event block graph" is defined as a graph that displays one or more event objects in a histogram format or a similar format. In one embodiment, event data 122 may be used as the secondary data 142 in an event block graph. In event block graph 1302, each event object is displayed as an event block, which is a visual representation of the event object. An event block can be any shape. For example, in event block graph 1302, each event block is represented as a square in a histogram. In event block graph 1302, each event block represents an event object that relates to a financial transaction from Dr. Smith. In one embodiment, a visual characteristic of an event block can be used to represent one or more criteria that is determined based on the event object. A visual characteristic of an event block can include the color, shape, size, shading, border, border color, opacity, transparency or any other visual characteristic of an event block. For example, in event block graph 1302, each event block represents the criteria of the value of the financial transaction based on the color of the event block. Financial transactions in the range of $0 and $10,000 are represented as one color, and financial transactions that are greater than $10,000 are represented as another color. An event block graph thus allows a user to easily identify particular event objects that satisfy one or more criteria. The criteria may be used to identify event objects that are suspicious. In one embodiment, the criteria for determining a visual characteristic of an event block can be configured via a user interface. By correlating the event block graph 1302 with the stack graph 1300, the system allows a user is to easily identify patterns between suspicious event objects in the event block graph 1302 with patterns displayed in the stack graph 1300.

In one embodiment, drawing system 100 may include multiple secondary drawing systems 130. Each secondary drawing system 130 can draw its own secondary table or secondary graph to be cross correlated against a stack graph. Thus, it would be possible to display a stack graph in conjunction with multiple secondary tables and/or secondary graphs.

Stack Line Clusters

Figure 6:
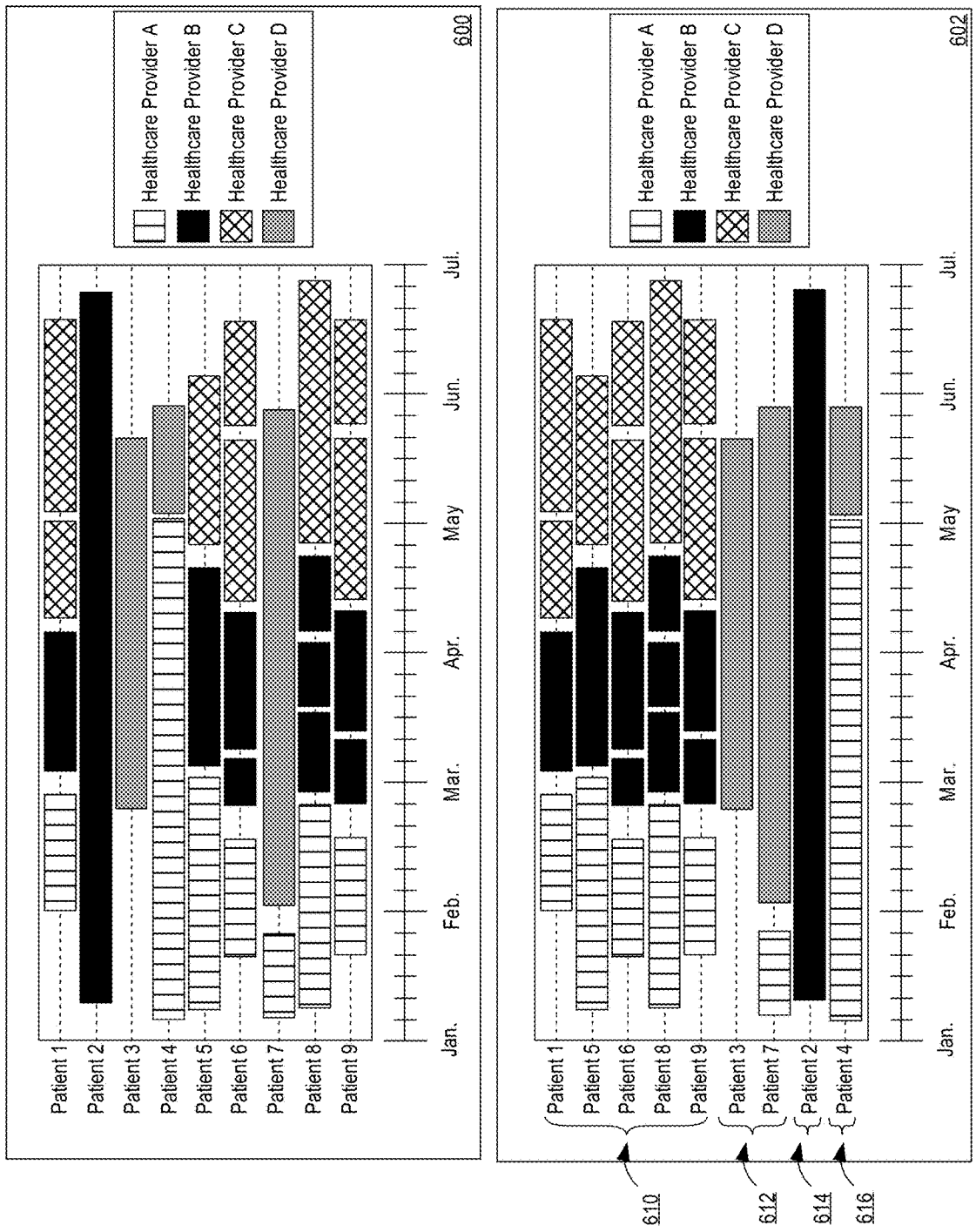
FIG. 6 is a diagram of example stack graphs.

In an embodiment, stack graph clustering logic 116 can group one or more stack lines of a stack graph into a stack line cluster to allow a user to more easily identify patterns in the underlying event data. A stack line cluster is a grouping of one or more stack lines in a stack graph that share a measure of similarity. For example, stack graph 600 in FIG. 6 is an unclustered stack graph that displays the stack lines for various event targets solely based on the alphabetized order of the stack line event target labels of the various stack lines. By comparison, stack graph 602 is a clustered stack graph that displays the stack lines for various event targets by grouping stack lines into stack line clusters using a clustering process of stack graph clustering logic 116. Stack line cluster 610 includes stack lines for Patients 1, 5, 6, 8 and 9. Stack line cluster 612 includes stack lines for Patients 3 and 7. Stack line cluster 614 includes a stack line for Patient 2. And stack line 616 includes a stack line for Patient 4. In stack graph 602, it is easier for a user to see that the stack lines associated with stack line cluster 610 all used Healthcare Provider A until approximately late February, then used Healthcare Provider B from early March until approximately mid-April, and then used Healthcare Provider C from mid-April onwards. By clustering the stack lines in a stack graph into stack line clusters, the patterns in the event data can be more easily identified.

Figure 7:
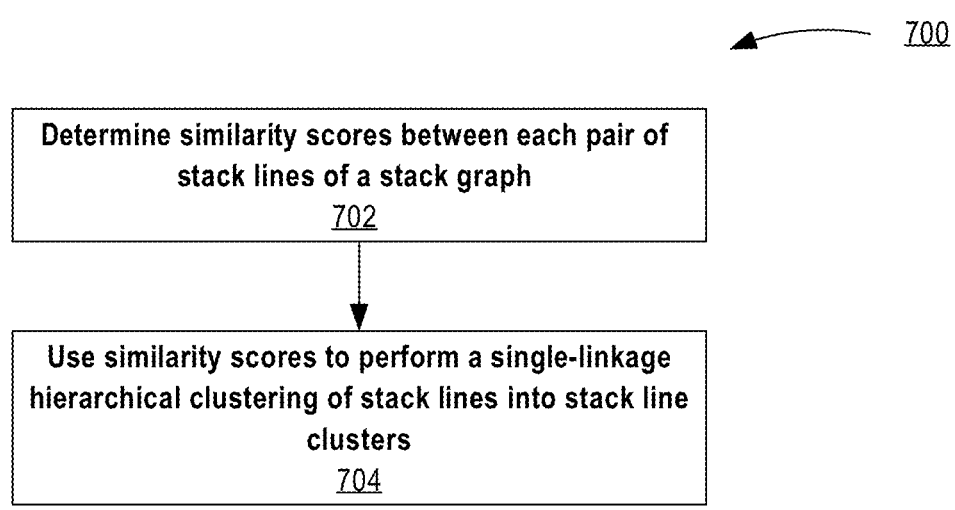
FIG. 7 is a flow diagram of an example clustering process.

FIG. 7 illustrates an example of a clustering process 700 of stack graph clustering logic 116 for creating stack line clusters. In step 702, stack graph distance logic 114 determines distance scores between each pair of stack lines in a stack graph and provides these distance scores to stack graph clustering logic 116. A distance score is a measure of the similarity of two stack lines. Stack graph distance logic 114 can determine a distance score between two stack lines using one of various techniques.

Figure 8:
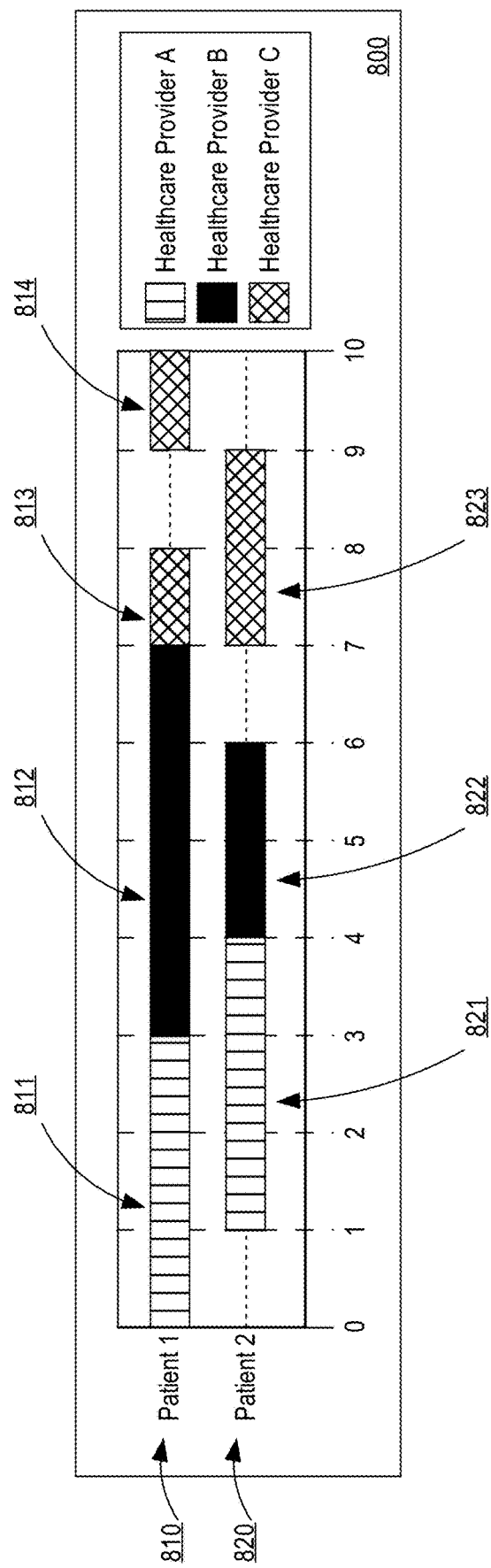
FIG. 8 is an example stack graph.

In one embodiment, stack graph distance logic 114 determines a shorthand representation of each stack line and uses the shorthand representations to determine a distance score between two stack lines. A shorthand representation of a stack line may comprise a data structure that includes characteristics that correlate with the pattern of event overlays on the stack line. In one embodiment, a shorthand representation of a stack line is a string. To illustrate, FIG. 8 shows a simplified example stack graph 800 with stack lines 810 and 820. Stack line 810 includes event overlays 811, 812, 813, and 814. Stack line 820 includes event overlays 821, 822, and 823.

One possible shorthand representation of a stack line is to create a string where each character of the string represents an event overlay in the stack line in chronological order based on the beginning of the event time data associated with the event overlay and where each character corresponds to the event source associated with the event overlay. Thus, a shorthand representation of stack line 810 could be "ABCC" and a shorthand representation of stack line 820 could be "ABC", where "A" indicates that Healthcare Provider A is the event source, "B" indicates that Healthcare Provider B is the event source, and so forth. In another embodiment, the shorthand representation is determined as before, but gaps in time where there are no event overlays in the stack line are shown as a different character in the shorthand representation, such as an underscore ("_"). Thus, a shorthand representation of stack line 810 could be "ABC_C" and a shorthand representation of stack line 820 could be "_AB_C_".

In another embodiment, a shorthand representation of a stack line is determined that collapses into a single character event sources of the same type that are not interrupted by another event overlay from an intervening event source. Thus, a shorthand representation of stack line 810 could be "ABC" and a shorthand representation of stack line 820 could be "ABC". In this example, event overlays 813 and 814 are collapsed into a single "C" character as there is no event overlay from an intervening event source between them.

In another embodiment, a shorthand representation of a stack line is determined whereby each character of the string represents a unit of time in the stack line in chronological order based on the event time data associated with the event overlay and where the character corresponds to the event source associated with the event overlay. Thus, a shorthand representation of stack line 810 could be "AAABBBBCC" and a shorthand representation of stack line 8202 could be "AAABBCC", where the number of contiguous identical characters indicates the period of time of the event overlay. For example, event overlay 811 can be represented as "AAA" as it occurs over three units of time. In another embodiment, the shorthand representation is determined as before, but gaps in time where there are no event overlays in the stack line are shown as a different character in the shorthand representation, such as an underscore ("_"). Thus, a shorthand representation of stack line 810 could be "AAABBBBC_C" and a shorthand representation of stack line 820 could be "_AAABB_CC_". The above examples of determining a shorthand representation of a stack line are merely exemplary, and other techniques may be used as well. Additionally, although the above examples describe an implementation using strings, a similar implementation of a shorthand representation can be done using similar data structures instead of literal strings.

In one embodiment, stack graph distance logic 114 can determine a distance score for the two stack lines using the shorthand representations. One technique for calculating a distance score between two stack lines is to determine a Jaccard index of the shingles of the shorthand representations. A Jaccard index, also known as a Jaccard coefficient, is a statistic used for comparing the similarity and diversity of sample sets. The Jaccard index measures similarity between finite sample sets, and may be defined as the size of the intersection of the sample sets, divided by the size of the union of the sample sets. A shingle or shingle set, also known as an n-gram, is a contiguous sequence of n entries from an array, where n is any integer value greater than zero. For example, in the case of a string, a shingle is a contiguous sequence of n characters from the string. In one embodiment, a shingle may be stored in a hash map or similar data structure, such that each duplicate contiguous sequences is only included once. For example, the string "AABCAA" may be converted into a shingle for n=2 (a "bigram"), represented as a hash map with the following contents: [AA, AB, BC, CA]. Likewise, the string "AABCAA" may be converted into a shingle for n=3 (a "trigram"), represented as a hash map with the following contents: [AAB, ABC, BCA, CAA]. Stack graph distance logic can determine a shingle for the shorthand representations of each of the two stack lines. Next, stack graph distance logic 114 determines a Jaccard index for the shingles for the two stack lines. The Jaccard index is a measure of the similarity between shingle sets. Thus, the Jaccard index of the shingles of the shorthand representations of the two stack lines may be used to determine the distance score of the two stack lines.

Another technique for calculating a distance score between two stack lines is to determine an edit distance between the shorthand representations of the stack lines. Edit distance measures the minimum number of operations (e.g., insertion, deletion, and/or substitution) required to transform one string into the other string. For example, in one embodiment, the edit distance between "good" and "food" may be represented as 1 (the substitution from "g" to "f"), while the edit distance between "good" and "goodbye" may be represented by 3 (the insertion of "b", "y", and "e"). Different algorithms for the calculation of edit distance may be used. For example, edit distance may be calculated as the Levenshtein distance, longest common subsequence (LCS) distance, Hamming distance, or Jaro-Winkler distance. Thus, the edit distance between the shorthand representations of the two stack lines may be used to determine the distance score of the two stack lines.

Another technique for calculating a distance score between two stack lines is to determine the temporal overlap between the stack lines. Temporal overlap is a measure of the amount of time that the two stack lines concurrently display event overlays wherein the event overlays are associated with the same event source. The amount of time can be measured as any unit of time, such as seconds, days, minutes, etc. In one embodiment, the temporal overlap is measured by iterating over the event overlays in each stack line of a pair of stack lines and determining the event overlap between such event overlay pairs. The logarithm of the result of the event overlap can be added to a running total temporal overlap for the two stack lines. The next iteration proceeds by advancing the iterator of the stack line that had an event overlay that was oldest in time to the next event overlay in the stack line.

Figure 9:
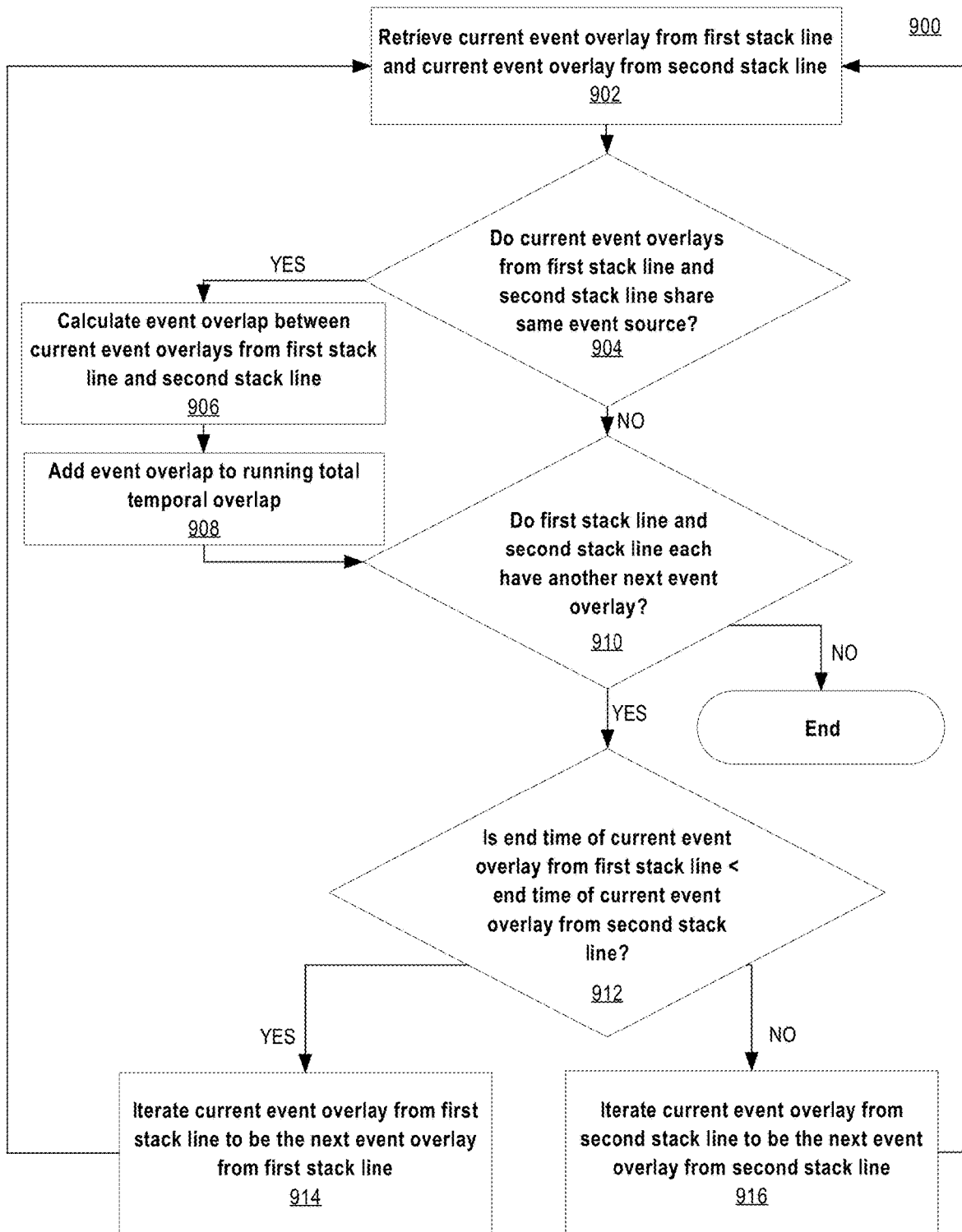
FIG. 9 is a flow diagram of an example process for calculating a temporal overlap between a pair of stack lines.

FIG. 9 shows a process 900 of calculating a temporal overlap for a first and second stack line that may be performed by stack graph distance logic 114, according to one embodiment. In step 902, the process 900 retrieves the current event overlay from the first stack line and the current event overlay from the second stack line, which, at the beginning of the process, is the first event overlay in chronological order in each stack line. The process 900 proceeds to step 904.

In step 904, the process 900 determines whether the current event overlay from the first stack line and the current event overlay from the second stack line share the same event source, as determined by analyzing the event objects associated with the event overlays. If the event overlays share the same event source, then the process 900 proceeds to step 906, otherwise, the process 900 proceeds to step 910.

In step 906, the process 900 calculates the event overlay between the current event overlay of the first stack line and the current event overlay of the second stack line. The event overlap represents the amount of time wherein two event overlays that share an event source are concurrently displayed. For example, in FIG. 8, the event overlap for event overlays 811 and 821 would be two units of time, the event overlap for event overlays 812 and 822 would be two units of time, and the event overlap for event overlays 813 and 823 would be one unit of time. Likewise, the event overlap for event overlays 821 and 812 would be zero, because the event overlays 821 and 812 have different event sources. The process 900 proceeds to step 908 after the event overlap is calculated.

In step 908, the process 900 adds the event overlap to a running total temporal overlap for the two stack lines. In one embodiment, in step 908, the process 900 adds the logarithm of the event overlap to the running total temporal overlap for the two stack lines. By using a logarithm of the event overlap instead of the absolute event overlap, the process 900 normalizes particularly large individual event overlap values so that they do not dominate the running total temporal overlap. The process 900 proceeds to step 910.

In step 910, the process 900 determines whether each of the first stack line and the second stack line have a next event overlay after the current event overlay. If not, the process may end. If both stack lines have a next event overlay, the process 900 proceeds to step 912.

In step 912, the process 900 determines if the end time of the current event overlay from the first stack line is less than the end time of the current event overlay of the second stack line. The end times can be determined by analyzing the event time data associated with the event object of the event overlay. If the end time of the current event overlay from the first stack line is less than the end time of the current event overlay from the second stack line, then the process 900 proceeds to step 914, otherwise, the process 900 proceeds to step 916. This step ensures that the iteration across the event overlays of the two stack lines occurs chronologically and in parallel.

In step 914, the process 900 iterates the current event overlay from the first stack line to be the next event overlay from the first stack line. The current event overlay from the second stack line is not modified. The process 900 then returns to step 902.

On the other hand, in step 916, the process 900 iterates the current event overlay from the second stack line to be the next event overlay from the first stack line. The current event overlay from the first stack line is not modified. The process 900 then returns to step 902.

In one embodiment, the running total temporal overlap is used to determine a distance score. For example, the running total temporal overlap may be used as the distance score. Alternatively, the running total temporal overlap is normalized by dividing the running total overlap by a normalization factor. The normalization factor may be calculated by summing the logarithm of all event durations from both stack lines.

Returning to FIG. 7, once the distance scores between each pair of stack lines of a stack graph is calculated in step 702, the clustering process 700 proceeds to step 704. In step 704, the stack graph clustering logic 116 uses the distance scores to perform a hierarchical clustering of stack lines of a stack graph into one or more stack line clusters. In one embodiment, the hierarchical clustering that is performed is single-linkage hierarchical clustering. Single-linkage hierarchical clustering is a type of agglomerative clustering ("bottom-up clustering"). In single-linkage hierarchical clustering, each stack line begins as a singleton stack line cluster at the bottom of a tree of clusters. Stack line clusters are iteratively combined into a tree of larger clusters, until all stack lines end up being in the same cluster at the highest level of the tree. At each iteration, the two clusters that are most similar, based on distance score, are combined into a larger cluster that is a parent of the two clusters. In single-linkage hierarchical clustering, the distance score between two clusters is determined to be the distance score between stack lines of each cluster that is the lowest. The result of the single-linkage clustering process is a dendrogram, or tree diagram, that can be used to determine an organization of stack line clusters for the stack graph in a sorted order. Stack graph drawing system 110 can display the stack line clusters on computer display unit 150.

In step 704, when combining two stack line clusters, stack graph clustering logic 116 may determine a cluster size for every stack line cluster of the stack graph. Cluster size is a measure of the number of stack lines in a stack line cluster. A high cluster size may indicate a pattern that exists across a large number of stack lines in the stack graph, therefore the cluster may be of particular interest to a user viewing the stack graph.

In step 704, when combining two stack line clusters, stack graph clustering logic 116 may determine a cohesiveness score for every stack line cluster of the stack graph. A cohesiveness score is a measure of the aggregate similarity of all of the stack lines in a stack line cluster. Stack graph clustering logic 116 may determine a total distance score for a stack line cluster. The total distance score of a stack line cluster is a value that represents the sum of the distance scores for each pair of stack lines in the stack line cluster. In one embodiment, the total distance score may be used as the cohesiveness score of the stack line cluster. In one embodiment, the total distance score may be used to calculate the cohesiveness score of the stack line cluster. For example, stack graph clustering logic 116 may determine an average distance score for the stack line cluster. The average distance score of a stack line cluster is a value that represents the average distance score between each pair of stack lines in the stack line cluster. The average distance score may be calculated as the total distance score of a stack line cluster divided by the number of unique pairs of stack lines in the stack line cluster. In an embodiment, the average distance score may be used as the cohesiveness score of the stack line cluster. In an embodiment, the cohesiveness score of a stack line cluster with only a single stack line is zero. Thus, a high cohesiveness score indicates that the stack lines in the stack line cluster are very similar to one another and a low cohesiveness score indicates that the stack lines in the stack line cluster are less similar to one another. A high cohesiveness score may be indicative that the stack lines in a stack line cluster are subject to a specific pattern and may be of particular interest to a user that is viewing the stack graph.

Additionally, in step 704, when combining two stack line clusters, stack graph clustering logic 116 may use the cluster size and/or the cluster cohesiveness score to determine a cluster interest score for every stack line cluster of the stack graph, where a cluster interest score is a value that represents how the stack line cluster should be sorted in the stack line graph based on estimating how "interesting" the stack line cluster may be to a user. As shown in FIG. 6, stack line cluster 610 is sorted to be the first displayed stack line cluster based on its cluster interest score, stack line cluster 612 is sorted to be the second displayed stack line cluster based on its cluster interest score, stack line cluster 614 is sorted to be the third displayed stack line cluster based on its cluster interest score, and stack line cluster 616 is sorted to be the fourth displayed stack line cluster based on its cluster interest score. In one embodiment, the cluster interest score of a stack line cluster is the cluster cohesiveness score, and cluster size may optionally be used to break ties. In another embodiment, the cluster interest score of a stack line cluster is the cluster size, and cluster cohesiveness score may optionally be used to break ties. In an embodiment, the cluster interest score of a stack line cluster is calculated based on a formula that is applied to the cluster cohesiveness score and the cluster size. For example, in one embodiment a value x can represent the cluster interest score and can be used to sort the stack graph clusters, where $x=c*s^{1/2}$, whereby c is the cluster cohesiveness score and s is the cluster size.

In step 704, stack graph clustering logic 116 may use the cluster interest score of the stack line clusters of the stack line graph to sort the order of the stack line clusters such that those stack line clusters with a higher cluster interest score are shown at the top of the stack line graph. The various routines performed by stack graph clustering logic 116 during step 704 described above may be performed simultaneously or in any order. Once step 704 is completed, the process 700 may end.

By displaying stack lines in stack line clusters, drawing system 100 makes it easier to identify patterns in the event data. For example, a cluster of stack lines may indicate that there is a pattern occurring across the stack lines of the stack line cluster. Furthermore, by sorting the stack line clusters based on a cluster interest score, drawing system 100 is able to prioritize those stack line clusters that may be more interesting for further analysis at the top of the stack graph, thereby enabling a user to quickly and easily identify stack line clusters that may be particularly interesting for further investigation.

Stack Graph Filtering

Figure 10:
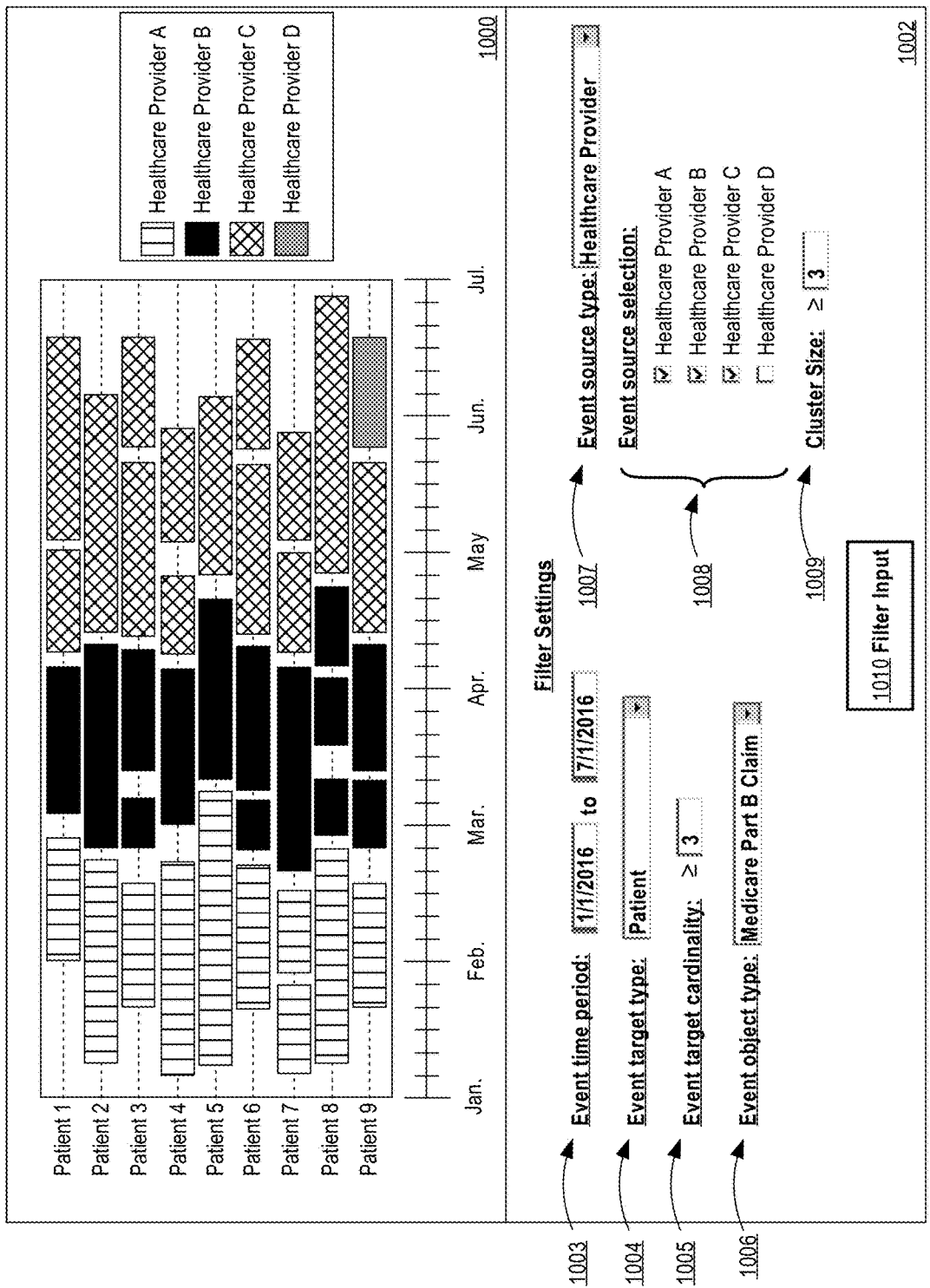
FIG. 10 is a diagram of an example stack graph and example filter graphical user interface.

In an embodiment, drawing system 100 may display a filter graphical user interface (GUI) in addition in addition to a stack graph. For example, in FIG. 10, drawing system 100 may display filter GUI 1002. Filter GUI 1002 is a user interface for collecting one or more filter settings based on user input. A filter setting is a user interface element for collecting a filter parameter that stack graph display logic 112 can use to modify the display of stack graph 1000. Filter settings may include an event time period 1003, event target type 1004, event target cardinality 1005, event object type 1006, event source type 1007, event source selection 1008, and/or cluster size 1009. Event time period 1003 collects a filter parameter that specifies a particular time period that should be displayed in the stack graph 1000. In FIG. 10, event time period 1003 specifies a time period of Jan. 1, 2016 to Jul. 1, 2016, which correlates with the time period shown in the timeline of stack graph 1000.

Event target type 1004 and event source type 1007 collect filter parameters that represents a characteristic of an event target or an event source, respectively, thereby allowing a user to specify a particular type of event target or event source to include or exclude from the stack graph 1000. The characteristics can be any characteristic of the event target or event source. For example, if an event target represents a person, an event target characteristic may be a gender of the person.

Event target cardinality 1005 collects a filter parameter that represents a cardinality setting that can limit the event targets that are displayed as a stack line in a stack graph 1000. The cardinality of an event target is the number of unique event sources associated with the event target via event objects. For example, in stack graph 1000, the event target for "Patient 1" has a cardinality of 3 because it has three unique event sources associated with it via event objects (Healthcare Providers A, B and C). By contrast, in stack graph 1000, the event target for "Patient 9" has a cardinality of 4 because it has four unique event sources associated with it via event objects (Healthcare Providers A, B, C and D). In event target cardinality 1005, all event targets that have a cardinality greater than or equal to 3 are being shown in stack graph 1000. In one embodiment, the stack graph 1000 may be filtered based on a default cardinality value that may be pre-configured for the stack graph drawing system 110. Cardinality is a useful tool for filtering the results in a stack graph because it allows a user to include or exclude, from a stack graph, those stack lines for event targets that do not have a high degree of variability in event sources. Such stack lines may, for example, have a low likelihood of containing a pattern that requires detection. In one embodiment, the event target cardinality is determined by stack graph display logic that analyzes the event data. In another embodiment, the event target cardinality is determined by secondary display logic that analyzes secondary data. In one embodiment, the event target cardinality is determined based on a secondary graph, wherein the secondary graph is a histogram.

Event object type 1006 collects a filter parameter that represents a characteristic of an event object, thereby allowing a user to specify a particular type of event object to include or exclude from the stack graph 1000. The characteristics can be any characteristic of the event object. For example, if an event object represents a healthcare Medicare claim, an event object type may be the specific type of Medicare claim (e.g. Medicare Part B Claim, Medicare Part C Claim, etc.)

Event source selection 1008 collects a filter parameter that specifies particular event sources that are to be included or excluded from the stack graph 1000. For example, in FIG. 10, event source selection 1008 indicates that Healthcare Provider D should be excluded from the stack graph 1000, while Healthcare Providers A, B, and C should be included in the stack graph 1000.

Cluster size 1009 collects a filter parameter that specifies the required cluster size of stack line clusters that are to be displayed in stack graph 1000. Including cluster size as a filter setting is helpful because it allows a user to narrow down the information in the stack graph to stack line clusters of a particular cluster size that may be relevant for the particular pattern they are trying to detect.

In an embodiment, filter GUI 1002 includes a filter input 1010, which is a user input, such as a button, that allows a user to apply the filter settings to the stack graph 1000. Stack graph display logic 112 can receive the user input and use the one or more filter settings to redraw the stack graph 1000 based on the filter parameters provided. Although FIG. 10 illustrates some exemplary filter settings 1003, 1004, 1005, 1006, 1007, 1008, and 1009 that may be included in a filter GUI 1002, any type of filter setting that relates to a characteristic of an event target, an event source, an event object, a timeline, a stack line, an event overlay, or a stack line cluster may be included. Additionally, filter settings may be implemented with any known GUI elements, including, but not limited to, buttons, touch gestures, checkboxes, radio buttons, text inputs, dropdown selections, dialog boxes, etc. Additionally, although filter GUI 1002 is shown in FIG. 10 as a separate settings panel than stack graph 1000, in another embodiment, one or more filter settings of filter GUI 1002 may be integrated directly into the stack graph 1000.

Stack graph display logic 112 can use filter settings to modify and manipulate the types of data displayed in stack graph 1000. In an embodiment, stack graph display logic 112 can use previously-stored default filter settings when a user has not input any filter settings.

Healthcare Fraud

One health care fraud scheme involves a medical practitioner, such as a doctor, referring a bundle of healthcare beneficiaries to a first healthcare provider in exchange for a financial kickback payment. The payment of a kickback is a type of fraud. In some cases, the same bundle of beneficiaries may then be subsequently transferred to a second healthcare provider in exchange for additional financial kickback payments to the medical practitioner or to the first home healthcare provider, thereby treating the bundle of beneficiaries as a transferable commodity. The trading of a bundle of patients as a transferable commodity amongst healthcare providers is another form of fraud. Detecting these forms of healthcare fraud can be challenging, as it requires identifying patterns of behavior amongst a small subset of healthcare claims from a larger superset of claims data.

In an embodiment, a stack graph can be used to help identify patterns of healthcare fraud. Referring back to FIG. 6, in an embodiment, each event target may represent a healthcare beneficiary, such as a patient. Each event source may represent a healthcare provider, such as a home healthcare provider or hospice care. Each event overlay may represent an event object, such as a healthcare claim, that describes a healthcare transaction or healthcare relationship between a particular healthcare beneficiary and a particular healthcare provider. For example, each event overlay may represent a Medicare Part B claim between a particular healthcare beneficiary and a particular healthcare provider. Thus, each stack line in stack graph 602 represents a pattern of healthcare received by a particular healthcare beneficiary over a time period across a variety of healthcare providers. The visualization of the stack graph allows a user to easily identify patterns of behavior amongst the various healthcare beneficiaries. Specifically, in stack graph 602, a user may be able to identify that the health care beneficiaries associated with stack line cluster 610 all received Healthcare Part B claims from Healthcare Provider A until approximately the end of February, at which point they all received Healthcare Part B claims from Healthcare Provider B until approximately the middle of April, at which point they all received Healthcare Part B claims from Healthcare Provider C. This trend may suggest to a user that the healthcare beneficiaries associated with stack line cluster 610 may have been treated as a bundle in a healthcare fraud scheme. The user can then further investigate as to whether there were any kickbacks paid by the healthcare providers to one another or a medical practitioner. In an embodiment, the user can cross correlate the information seen in stack graph 602 against a secondary graph or secondary table that represents financial transaction data in order to determine whether any kickbacks were paid to a medical practitioner or a healthcare provider in a temporally relevant way. For example, a user can use a stack graph and a secondary graph to see if kickbacks are paid from Healthcare Provider B to Healthcare Provider A at the same time as patients move between the two healthcare providers, as represented by the claims data.

Insider Trading

Insider trading is a practice of financial trading whereby a trader places a trade to their advantage based on non-public information. Insider trader is oftentimes illegal and it would be beneficial to be able to easily identify when insider trading occurs.

In an embodiment, a stack graph can be used to help identify insider trading. For example, in one embodiment, each event target may represent a trader. Likewise, each event source may represent a financial product or financial instrument, such as a stock or a bond. Each event object may represent a financial transaction whereby a trader (e.g., an event target) purchases or sells a particular financial product or financial instrument (e.g., an event source). Thus, each stack line in a stack graph represents a pattern of financial transactions performed by a trader over time. In an embodiment, such a stack graph could be displayed with a secondary graph or secondary table that shows communication data that represents communications received from a source of confidential information, such as an employee. Communications may include telephone call logs, emails, text messages, letters, and other forms of communication. A user could thereby cross correlate the pattern of financial transactions shown in the stack graph with the communication data shown in the secondary graph or secondary table in order to identify patterns indicative of insider trading. For example, if a user can see communications to one or more traders at the same time that the trader(s) performed financial transactions, the user could identify the trader(s) as potentially being involved in insider trading.

Basic Computing Device

Figure 11:
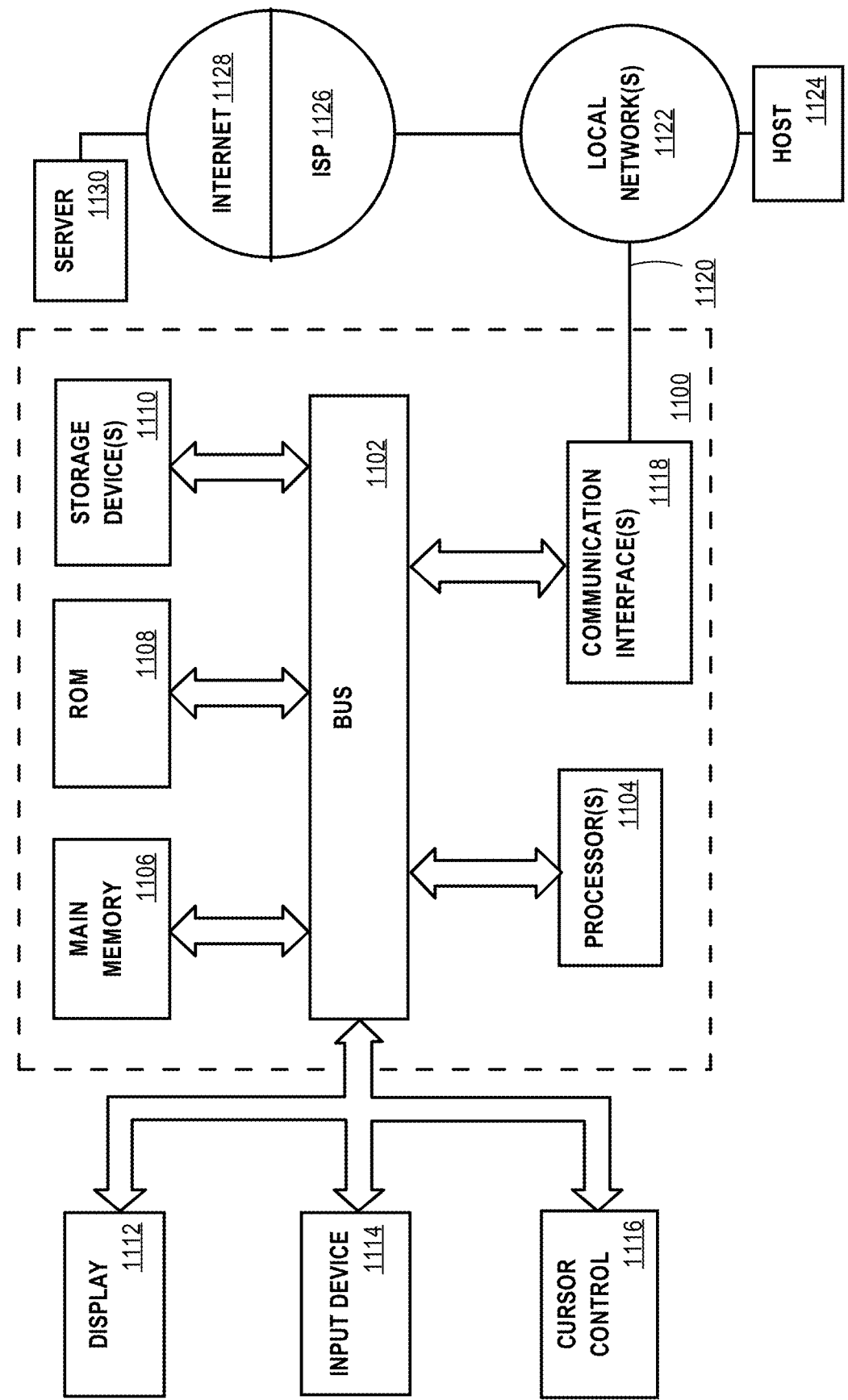
FIG. 11 is a block diagram of a computing device in which the example embodiment(s) of the present invention may be embodied.

Referring now to FIG. 11, it is a block diagram that illustrates a basic computing device 1100 in which the example embodiment(s) of the present invention may be embodied. Computing device 1100 and its components, including their connections, relationships, and functions, is meant to be exemplary only, and not meant to limit implementations of the example embodiment(s). Other computing devices suitable for implementing the example embodiment(s) may have different components, including components with different connections, relationships, and functions.

Computing device 1100 may include a bus 1102 or other communication mechanism for addressing main memory 1106 and for transferring data between and among the various components of device 1100.

Computing device 1100 may also include one or more hardware processors 1104 coupled with bus 1102 for processing information. A hardware processor 1104 may be a general purpose microprocessor, a system on a chip (SoC), or other processor.

Main memory 1106, such as a random access memory (RAM) or other dynamic storage device, also may be coupled to bus 1102 for storing information and software instructions to be executed by processor(s) 1104. Main memory 1106 also may be used for storing temporary variables or other intermediate information during execution of software instructions to be executed by processor(s) 1104.

Software instructions, when stored in storage media accessible to processor(s) 1104, render computing device 1100 into a special-purpose computing device that is customized to perform the operations specified in the software instructions. The terms "software", "software instructions", "computer program", "computer-executable instructions", and "processor-executable instructions" are to be broadly construed to cover any machine-readable information, whether or not human-readable, for instructing a computing device to perform specific operations, and including, but not limited to, application software, desktop applications, scripts, binaries, operating systems, device drivers, boot loaders, shells, utilities, system software, JAVASCRIPT, web pages, web applications, plugins, embedded software, microcode, compilers, debuggers, interpreters, virtual machines, linkers, and text editors.

Computing device 1100 also may include read only memory (ROM) 1108 or other static storage device coupled to bus 1102 for storing static information and software instructions for processor(s) 1104.

One or more mass storage devices 1110 may be coupled to bus 1102 for persistently storing information and software instructions on fixed or removable media, such as magnetic, optical, solid-state, magnetic-optical, flash memory, or any other available mass storage technology. The mass storage may be shared on a network, or it may be dedicated mass storage. Typically, at least one of the mass storage devices 1110 (e.g., the main hard disk for the device) stores a body of program and data for directing operation of the computing device, including an operating system, user application programs, driver and other support files, as well as other data files of all sorts.

Computing device 1100 may be coupled via bus 1102 to display 1112, such as a liquid crystal display (LCD) or other electronic visual display, for displaying information to a computer user. In some configurations, a touch sensitive surface incorporating touch detection technology (e.g., resistive, capacitive, etc.) may be overlaid on display 1112 to form a touch sensitive display for communicating touch gesture (e.g., finger or stylus) input to processor(s) 1104.

An input device 1114, including alphanumeric and other keys, may be coupled to bus 1102 for communicating information and command selections to processor 1104. In addition to or instead of alphanumeric and other keys, input device 1114 may include one or more physical buttons or switches such as, for example, a power (on/off) button, a "home" button, volume control buttons, or the like.

Another type of user input device may be a cursor control 1116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane.

While in some configurations, such as the configuration depicted in FIG. 11, one or more of display 1112, input device 1114, and cursor control 1116 are external components (e.g., peripheral devices) of computing device 1100, some or all of display 1112, input device 1114, and cursor control 1116 are integrated as part of the form factor of computing device 1100 in other configurations.

Functions of the disclosed systems, methods, and modules may be performed by computing device 1100 in response to processor(s) 1104 executing one or more programs of software instructions contained in main memory 1106. Such software instructions may be read into main memory 1106 from another storage medium, such as storage device(s) 1110. Execution of the software instructions contained in main memory 1106 cause processor(s) 1104 to perform the functions of the example embodiment(s).

While functions and operations of the example embodiment(s) may be implemented entirely with software instructions, hard-wired or programmable circuitry of computing device 1100 (e.g., an ASIC, a FPGA, or the like) may be used in other embodiments in place of or in combination with software instructions to perform the functions, according to the requirements of the particular implementation at hand.

The term "storage media" as used herein refers to any non-transitory media that store data and/or software instructions that cause a computing device to operate in a specific fashion. Such storage media may comprise non-volatile media and/or volatile media. Non-volatile media includes, for example, non-volatile random access memory (NVRAM), flash memory, optical disks, magnetic disks, or solid-state drives, such as storage device 1110. Volatile media includes dynamic memory, such as main memory 1106. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, flash memory, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1102. Transmission media can also take the form of acoustic or light waves, such as those generated during radio-wave and infra-red data communications.

Various forms of media may be involved in carrying one or more sequences of one or more software instructions to processor(s) 1104 for execution. For example, the software instructions may initially be carried on a magnetic disk or solid-state drive of a remote computer. The remote computer can load the software instructions into its dynamic memory and send the software instructions over a telephone line using a modem. A modem local to computing device 1100 can receive the data on the telephone line and use an infra-red transmitter to convert the data to an infra-red signal. An infra-red detector can receive the data carried in the infra-red signal and appropriate circuitry can place the data on bus 1102. Bus 1102 carries the data to main memory 1106, from which processor(s) 1104 retrieves and executes the software instructions. The software instructions received by main memory 1106 may optionally be stored on storage device(s) 1110 either before or after execution by processor(s) 1104.

Computing device 1100 also may include one or more communication interface(s) 1118 coupled to bus 1102. A communication interface 1118 provides a two-way data communication coupling to a wired or wireless network link 1120 that is connected to a local network 1122 (e.g., Ethernet network, Wireless Local Area Network, cellular phone network, Bluetooth wireless network, or the like). Communication interface 1118 sends and receives electrical, electromagnetic, or optical signals that carry digital data streams representing various types of information. For example, communication interface 1118 may be a wired network interface card, a wireless network interface card with an integrated radio antenna, or a modem (e.g., ISDN, DSL, or cable modem).

Network link(s) 1120 typically provide data communication through one or more networks to other data devices. For example, a network link 1120 may provide a connection through a local network 1122 to a host computer 1124 or to data equipment operated by an Internet Service Provider (ISP) 1126. ISP 1126 in turn provides data communication services through the world wide packet data communication network now commonly referred to as the "Internet" 1128. Local network(s) 1122 and Internet 1128 use electrical, electromagnetic or optical signals that carry digital data streams. The signals through the various networks and the signals on network link(s) 1120 and through communication interface(s) 1118, which carry the digital data to and from computing device 1100, are example forms of transmission media.

Computing device 1100 can send messages and receive data, including program code, through the network(s), network link(s) 1120 and communication interface(s) 1118. In the Internet example, a server 1130 might transmit a requested code for an application program through Internet 1128, ISP 1126, local network(s) 1122 and communication interface(s) 1118.

The received code may be executed by processor 1104 as it is received, and/or stored in storage device 1110, or other non-volatile storage for later execution.

Basic Software System

Figure 12:
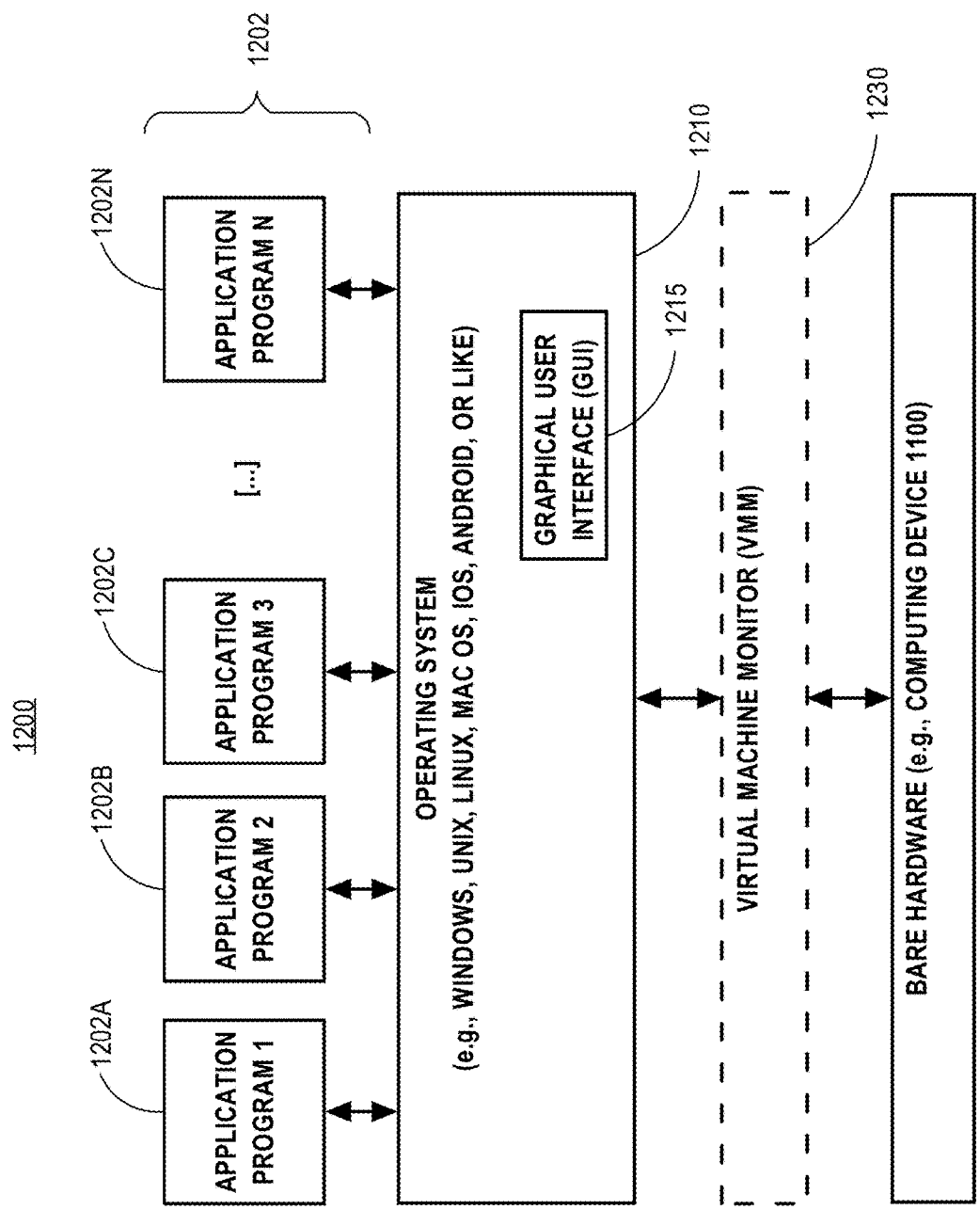
FIG. 12 is a block diagram of a software system for controlling the operation of the computing device.

FIG. 12 is a block diagram of a basic software system 1200 that may be employed for controlling the operation of computing device 1100. Software system 1200 and its components, including their connections, relationships, and functions, is meant to be exemplary only, and not meant to limit implementations of the example embodiment(s). Other software systems suitable for implementing the example embodiment(s) may have different components, including components with different connections, relationships, and functions.

Software system 1200 is provided for directing the operation of computing device 1100. Software system 1200, which may be stored in system memory (RAM) 1106 and on fixed storage (e.g., hard disk or flash memory) 1110, includes a kernel or operating system (OS) 1210.

The OS 1210 manages low-level aspects of computer operation, including managing execution of processes, memory allocation, file input and output (I/O), and device I/O. One or more application programs, represented as 1202A, 1202B, 1202C . . . 1202N, may be "loaded" (e.g., transferred from fixed storage 1110 into memory 1106) for execution by the system 1200. The applications or other software intended for use on device 1200 may also be stored as a set of downloadable computer-executable instructions, for example, for downloading and installation from an Internet location (e.g., a Web server, an app store, or other online service).

Software system 1200 includes a graphical user interface (GUI) 1215, for receiving user commands and data in a graphical (e.g., "point-and-click" or "touch gesture") fashion. These inputs, in turn, may be acted upon by the system 1200 in accordance with instructions from operating system 1210 and/or application(s) 1202. The GUI 1215 also serves to display the results of operation from the OS 1210 and application(s) 1202, whereupon the user may supply additional inputs or terminate the session (e.g., log off).

OS 1210 can execute directly on the bare hardware 1220 (e.g., processor(s) 1104) of device 1100. Alternatively, a hypervisor or virtual machine monitor (VMM) 1230 may be interposed between the bare hardware 1220 and the OS 1210. In this configuration, VMM 1230 acts as a software "cushion" or virtualization layer between the OS 1210 and the bare hardware 1220 of the device 1100.

VMM 1230 instantiates and runs one or more virtual machine instances ("guest machines"). Each guest machine comprises a "guest" operating system, such as OS 1210, and one or more applications, such as application(s) 1202, designed to execute on the guest operating system. The VMM 1230 presents the guest operating systems with a virtual operating platform and manages the execution of the guest operating systems.

In some instances, the VMM 1230 may allow a guest operating system to run as if it is running on the bare hardware 1220 of device 1100 directly. In these instances, the same version of the guest operating system configured to execute on the bare hardware 1220 directly may also execute on VMM 1230 without modification or reconfiguration. In other words, VMM 1230 may provide full hardware and CPU virtualization to a guest operating system in some instances.

In other instances, a guest operating system may be specially designed or configured to execute on VMM 1230 for efficiency. In these instances, the guest operating system is "aware" that it executes on a virtual machine monitor. In other words, VMM 1230 may provide para-virtualization to a guest operating system in some instances.

The above-described basic computer hardware and software is presented for purpose of illustrating the basic underlying computer components that may be employed for implementing the example embodiment(s). The example embodiment(s), however, are not necessarily limited to any particular computing environment or computing device configuration. Instead, the example embodiment(s) may be implemented in any type of system architecture or processing environment that one skilled in the art, in light of this disclosure, would understand as capable of supporting the features and functions of the example embodiment(s) presented herein.

Extensions and Alternatives

The systems and/or processing methods described herein improve the ability to identify patterns in a large set of event data. This can allow a user to narrow their analysis on a subset of data that displays a pattern. The techniques described can be used on any set of event data that includes a temporal aspect. In particular, the techniques are helpful in identifying fraud, such as healthcare fraud, insider trading, identity theft, etc. However, the techniques can also be in any other practical application area, including those that are unrelated to fraud. For example, the techniques described herein can be used to help detect security threats, to perform legal document review, or other various application areas.

In the foregoing specification, the example embodiment(s) of the present invention have been described with reference to numerous specific details. However, the details may vary from implementation to implementation according to the requirements of the particular implement at hand. The example embodiment(s) are, accordingly, to be regarded in an illustrative rather than a restrictive sense.

The invention claimed is:

1. A method comprising:
receiving a set of event data, wherein the set of event data comprises:
a plurality of event targets;
a plurality of event sources;
a plurality of event objects, wherein an event object corresponds to an event target of the plurality of event targets and an event source of the plurality of event sources;
displaying a group of stack lines along a timeline;
determining a cardinality of each event target of the plurality of event targets, each event target corresponding to a stack line of the group of stack lines, by:
identifying one or more particular event objects that correspond to a particular event target;
identifying one or more particular event sources that correspond to the one or more particular event objects;
counting a number of the one or more particular event sources that corresponds to the one or more particular event objects to determine the cardinality;
generating a cluster hierarchy of the plurality of event targets by:
calculating, for each event target of the plurality of event targets, a cohesiveness score based on a similarity of each event target of the plurality of event targets to an aggregate similarity of the plurality of event targets;
placing each event target of the plurality of event targets into the cluster hierarchy based on the cohesiveness scores, wherein placing each event target of the plurality of event targets into the cluster hierarchy comprises placing one or more event targets having a higher cluster score higher in the cluster hierarchy;
excluding, from the timeline, particular stack lines of the group of stack lines corresponding to a first group of event targets having a particular cardinality below a cardinality threshold;
modifying a displayed position of the remaining stack lines corresponding to a second group of event targets having a particular cardinality at or above the cardinality threshold, on the timeline, based, at least in part, on the cluster hierarchy;
wherein the method is executed using one or more processors.

2. The method of claim 1, wherein each stack line of the group of stack lines comprises one or more event overlays, the one or more event overlays each comprising:
a graphical representation of a particular event object that corresponds to the particular event target corresponding to a particular stack line; and
a visual characteristic that identifies a particular event source that corresponds to the particular event object.

3. The method of claim 2, wherein the visual characteristic comprises color-coding.

4. The method of claim 2, wherein each particular event overlay corresponds to a particular position on a respective stack line of the group of stack lines that is determined based on particular event time data of the one or more particular event objects corresponding to the particular event target corresponding to the respective stack line of the group of stack lines.

5. The method of claim 1, further comprising:
displaying a secondary graph based on a second set of data, wherein the secondary graph is correlated to the timeline based on time.

6. The method of claim 1, further comprising:
determining a distance score between a first stack line of the group of stack lines and a second stack line of the group of stack lines; and
grouping the first stack line and the second stack line into a stack line cluster based on analyzing the distance score.

7. The method of claim 6, wherein determining the distance score between the first stack line of the group of stack lines and the second stack line of the group of stack lines comprises determining a temporal overlap between the first stack line and the second stack line.

8. The method of claim 6, wherein determining the distance score between the first stack line of the group of stack lines and the second stack line of the group of stack lines comprises:
determining a first shingle based on analyzing the first stack line of the group of stack lines;
determining a second shingle based on analyzing the second stack line of the group of stack lines; and
determining a Jaccard index between the first shingle and the second shingle.

9. The method of claim 1, wherein:
the event target further comprises healthcare beneficiary data;
the event source further comprises healthcare provider data; and
the event object further comprises healthcare transaction data.

10. The method of claim 1, wherein:
the event target further comprises financial trader data;
the event source further comprises financial instrument data; and
the event object further comprises financial transaction data.

11. A system, comprising:
storage media;
one or more processors;
and one or more programs stored in the storage media and configured for execution by the one or more processors, the one or more programs comprising instructions for:
receiving a set of event data, wherein the set of event data comprises:
a plurality of event targets;
a plurality of event sources;
a plurality of event objects, wherein an event object corresponds to an event target of the plurality of event targets and an event source of the plurality of event sources;
displaying a group of stack lines along a timeline;
determining a cardinality of each event target of the plurality of event targets, each event target corresponding to a stack line of the group of stack lines, by:

identifying one or more particular event objects that correspond to a particular event target;

identifying one or more particular event sources that correspond to the one or more particular event objects;

counting a number of the one or more particular event sources that corresponds to the one or more particular event objects to determine the cardinality;

generating a cluster hierarchy of the plurality of event targets by:

calculating, for each event target of the plurality of event targets, a cohesiveness score based on a similarity of each event target of the plurality of event targets to an aggregate similarity of the plurality of event targets;

placing each event target of the plurality of event targets into the cluster hierarchy based on the cohesiveness scores, wherein placing each event target of the plurality of event targets into the cluster hierarchy comprises placing one or more event targets having a higher cluster score higher in the cluster hierarchy;

excluding, from the timeline, particular stack lines of the group of stack lines corresponding to a first group of event targets having a particular cardinality below a cardinality threshold;

modifying a displayed position of the remaining stack lines corresponding to a second group of event targets having a particular cardinality at or above the cardinality threshold, on the timeline, based, at least in part, on the cluster hierarchy.

12. The system of claim 11, wherein each stack line of the group of stack lines comprises one or more event overlays, the one or more event overlays each comprising:

a graphical representation of a particular event object that corresponds to the particular event target corresponding to a particular stack line; and a visual characteristic that identifies a particular event source that corresponds to the particular event object.

13. The system of claim 12, wherein the visual characteristic comprises color-coding.

14. The system of claim 12, wherein each particular event overlay corresponds to a particular position on a respective stack line of the group of stack lines that is determined based on particular event time data of the one or more particular event objects corresponding to the particular event target corresponding to the respective stack line of the group of stack lines.

15. The system of claim 11, further comprising instructions for:

displaying a secondary graph based on a second set of data, wherein the secondary graph is correlated to the timeline based on time.

16. The system of claim 11, further comprising instructions for:

determining a distance score between a first stack line of the group of stack lines and a second stack line of the group of stack lines; and grouping the first stack line and the second stack line into a stack line cluster based on analyzing the distance score.

17. The system of claim 16, wherein determining the distance score between the first stack line of the group of stack lines and the second stack line of the group of stack lines comprises determining a temporal overlap between the first stack line and the second stack line.

18. The system of claim 16, wherein determining the distance score between the first stack line of the group of stack lines and the second stack line of the group of stack lines comprises:

determining a first shingle based on analyzing the first stack line of the group of stack lines;

determining a second shingle based on analyzing the second stack line of the group of stack lines; and determining a Jaccard index between the first shingle and the second shingle.

19. The system of claim 11, wherein:

the event target further comprises healthcare beneficiary data;

the event source further comprises healthcare provider data; and the event object further comprises healthcare transaction data.

20. The system of claim 11, wherein:

the event target further comprises financial trader data;

the event source further comprises financial instrument data; and the event object further comprises financial transaction data.

* * * * *